(12) United States Patent
Nakaoka et al.

(10) Patent No.: US 9,079,163 B2
(45) Date of Patent: Jul. 14, 2015

(54) CATALYST AND METHOD FOR PRODUCING THE SAME AND METHOD FOR PRODUCING PARAXYLENE USING THE SAME

(75) Inventors: Chikanori Nakaoka, Tokyo (JP); Eri Kosaka, Tokyo (JP)

(73) Assignee: JX NIPPON OIL & ENERGY CORPORATION, Tokyo (JP)

(*) Notice: Subject to any disclaimer, the term of this patent is extended or adjusted under 35 U.S.C. 154(b) by 0 days.

(21) Appl. No.: 13/637,576

(22) PCT Filed: Mar. 16, 2011

(86) PCT No.: PCT/JP2011/057067
§ 371 (c)(1),
(2), (4) Date: Nov. 29, 2012

(87) PCT Pub. No.: WO2011/118668
PCT Pub. Date: Sep. 29, 2011

(65) Prior Publication Data
US 2013/0072736 A1 Mar. 21, 2013

(30) Foreign Application Priority Data
Mar. 26, 2010 (JP) ................................ 2010-073756

(51) Int. Cl.
| | |
|---|---|
| B01J 29/06 | (2006.01) |
| C07C 2/66 | (2006.01) |
| C07C 6/12 | (2006.01) |
| B01J 29/80 | (2006.01) |
| B01J 29/40 | (2006.01) |
| C07C 15/08 | (2006.01) |
| B01J 37/02 | (2006.01) |
| B01J 35/00 | (2006.01) |
| B01J 35/02 | (2006.01) |
| B82Y 40/00 | (2011.01) |
| B01J 37/03 | (2006.01) |

(52) U.S. Cl.
CPC ........ *B01J 29/80* (2013.01); *B01J 29/40* (2013.01); *B01J 35/002* (2013.01); *B01J 35/006* (2013.01); *B01J 35/023* (2013.01); *B01J 37/0221* (2013.01); *B01J 37/0246* (2013.01); *C07C 2/66* (2013.01); *C07C 6/123* (2013.01); *C07C 15/08* (2013.01); *B01J 37/035* (2013.01); *B82Y 40/00* (2013.01); *C07C 2529/70* (2013.01); *Y10S 977/773* (2013.01); *Y10S 977/896* (2013.01)

(58) Field of Classification Search
USPC ......... 502/63, 64, 67, 69, 71, 527.14, 527.15, 502/527.24; 977/773, 775; 585/467, 471, 585/475, 470
See application file for complete search history.

(56) References Cited

U.S. PATENT DOCUMENTS

| | | | |
|---|---|---|---|
| 4,088,605 A | 5/1978 | Rollmann | |
| 4,465,886 A | 8/1984 | Rodewald | |
| 4,748,291 A * | 5/1988 | Debras et al. ................. | 585/418 |
| 4,868,146 A | 9/1989 | Chu et al. | |
| 5,993,642 A | 11/1999 | Mohr et al. | |
| 5,994,603 A | 11/1999 | Mohr et al. | |
| 6,268,542 B1 * | 7/2001 | Merrill et al. ................. | 585/643 |
| 6,811,684 B2 | 11/2004 | Mohr et al. | |
| 7,446,071 B2 * | 11/2008 | Abrevaya et al. ............... | 502/67 |
| 2002/0082460 A1 * | 6/2002 | Verduijn et al. ............... | 585/475 |
| 2003/0121827 A1 | 7/2003 | van den Berge et al. | |
| 2004/0198586 A1 | 10/2004 | Mohr et al. | |
| 2005/0143613 A1 | 6/2005 | Dakka et al. | |
| 2007/0179043 A1 | 8/2007 | Kojima | |
| 2009/0012338 A1 | 1/2009 | Dakka et al. | |
| 2011/0009682 A1 * | 1/2011 | Matsushita et al. ........... | 585/321 |
| 2011/0190561 A1 * | 8/2011 | Bulut et al. .................... | 585/467 |
| 2012/0004487 A1 | 1/2012 | Igarashi et al. | |

FOREIGN PATENT DOCUMENTS

| | | |
|---|---|---|
| JP | A-63-240943 | 10/1988 |
| JP | B2-64-6816 | 2/1989 |
| JP | A-11-501286 | 2/1999 |
| JP | A-2001-504084 | 3/2001 |
| JP | A-2003-500189 | 1/2003 |
| JP | A-2003-62466 | 3/2003 |
| JP | A-2007-517030 | 6/2007 |
| JP | A-2007-203209 | 8/2007 |
| JP | A-2008-094685 | 4/2008 |
| JP | A-2008-126131 | 6/2008 |
| WO | WO 2006/033328 A1 | 3/2006 |
| WO | WO 2009/119725 A1 | 10/2009 |
| WO | WO 2009119725 A1 * | 10/2009 |
| WO | WO 2010/041573 A1 | 4/2010 |
| WO | WO 2010/107076 A1 | 9/2010 |

OTHER PUBLICATIONS

Lobo et al., "Structure-Direction in Zeolite Synthesis," *Journal of Inclusion Phenomena and Molecular Recognition in Chemistry*, (1995), vol. 21, pp. 47-78.

Jul. 5, 2011 Written Opinion of the International Searching Authority issued in International Application No. PCT/JP2011/057067 (with translation).

Oct. 23, 2012 International Preliminary Report on Patentability issued in International Application No. PCT/JP2011/057067 (with translation).

Jul. 5, 2011 International Search Report issued in International Application No. PCT/JP2011/057067 (with translation).

(Continued)

*Primary Examiner* — Elizabeth Wood
(74) *Attorney, Agent, or Firm* — Oliff PLC (57) ABSTRACT

The present invention relates to a novel catalyst which has a molecular sieving effect (or shape selectivity) and has excellent catalytic activity, and particularly to a catalyst which includes a core made of a zeolite particle having a particle size of not more than 10 μm and a zeolite layer covering the core, wherein as measured by X-ray photoelectron spectroscopy, an outermost surface of the catalyst has a silica/alumina molar ratio of not less than 800, the core made of the zeolite particle has an average silica/alumina molar ratio of not more than 300, and the zeolite layer has an aluminum concentration increasing inward from an outer surface of the catalyst.

7 Claims, 5 Drawing Sheets

(56) References Cited

OTHER PUBLICATIONS

Jan. 21, 2014 Notification of Reasons for Refusal issued in Japanese Application No. 2011-504875 (with English-language Translation).
May 25, 2010 International Search Report issued in Application No. PCT/JP2010/054615 (with English translation).
Sep. 19, 2013 Office Action issued in U.S. Appl. No. 13/256,060.
Apr. 28, 2014 Office Action issued in U.S. Appl. No. 13/256,060.
Sep. 12, 2014 Office Action issued in U.S. Appl. No. 13/256,060.
Wang et al., "Oriented films of epitaxial MFI overgrowths," Microporous and Mesoporous Materials 95 (2006), pp. 86-91.
Nov. 11, 2014 Official Decision of Refusal issued in Japanese Application No. 2010-073756.
Apr. 16, 2015 Office Action issued in U.S. Appl. No. 13/256,060.

* cited by examiner

CATALYST AND METHOD FOR PRODUCING THE SAME AND METHOD FOR PRODUCING PARAXYLENE USING THE SAME

TECHNICAL FIELD

The present invention relates to a synthetic zeolite catalyst and a method for producing the same and a method for producing high purity paraxylene using the catalyst, and particularly to a method for producing high purity paraxylene in an efficient manner by using a synthetic zeolite catalyst, in which an aluminum concentration gradient in a vicinity of an outer surface of the catalyst is controlled, extremely high selectivity in paraxylene synthesis is achieved, and isomerization activity of the paraxylene as a product is suppressed.

BACKGROUND ART

Among aromatic compounds, xylenes are very important compounds as starting materials for producing terephthalic acid, isophthalic acid, orthophthalic acid and so on, which are raw materials of polyester. While the xylenes are produced by, e.g., transalkylation, disproportionation reaction and so on of toluene, the product involves structural isomers of p-xylene, o-xylene and m-xylene. Terephthalic acid, which is obtained by oxidation of p-xylene, is used as a main raw material of polyethylene terephthalate; phthalic anhydride, which is obtained from o-xylene, is used as a raw material of plasticizers and so on; and isophthalic acid, which is obtained from m-xylene, is used as a main raw material of unsaturated polyesters and so on, respectively. Accordingly, there is a need for a method for separating these structural isomers from the product in an efficient manner.

However, there is little difference among the boiling points of p-xylene (with a boiling point of 138° C.), o-xylene (with a boiling point of 144° C.) and m-xylene (with a boiling point of 139° C.). This makes it difficult to separate these isomers by means of a normal distillation method. In response, there are methods for separating these isomers, such as a crystallization separation method where xylene mixture containing p-, o- and m-isomers is precisely distilled, which is then subjected to cooling crystallization to separate p-xylene with a high melting point, and a method for adsorbing and separating p-xylene using a zeolite-based adsorbent having a molecular sieving effect.

Such a method, where p-xylene is selectively separated by means of crystallization separation, is problematic in that the xylene mixture containing structural isomers must be subjected to precise distillation and then cooling crystallization, which results in a multi-stage, and thus more complicated process, and in that the precise distillation and cooling crystallization process lead to an increased production cost, etc. Accordingly, in place of this method, the adsorption and separation method has been most widely used. This method is of the type where p-xylene with stronger adsorbability than the other isomers is adsorbed and separated from the other isomers, while the xylene mixture as the raw material passes through the adsorption tower which is loaded with an adsorbent. Then, p-xylene is extracted from the system using a desorption agent. After the desorption, the p-xylene is separated from the desorption liquid through distillation. Practical processes include the PAREX process by UOP, AROMAX process by Toray and so on. This adsorption and separation method provides a high yield and high purity of p-xylene relative to the other separation methods. However, this method requires repeating adsorption and desorption sequentially using an adsorption tower with a pseudo-moving bed having 10 to 20-odd stages, and separately separating and removing the desorption agent for removing p-xylene from the adsorbent. As such, this method has offered by no means sufficient operating efficiency for the production of high purity p-xylene.

In contrast to this inefficient process, some attempts have been made by those skilled in the art to drastically improve the production efficiency of paraxylene. Specific examples include a method for producing paraxylene by selective methylation of toluene and so on. In this case, the methylation of toluene includes the production of paraxylene/benzene by disproportionation reaction of toluene itself. For example, Patent Document 1 listed below discloses a zeolite bound zeolite catalyst that comprises a first zeolite crystal having catalytic activity and a second zeolite crystal having a molecular sieving effect. However, in the zeolite bound zeolite catalyst disclosed in Patent Document 1, the second zeolite crystal having the molecular sieving effect forms a continuous phase matrix or bridge, and hence the proportion of the first zeolite crystal having the catalytic activity occupied in the zeolite bound zeolite catalyst becomes small, which results in decreased catalytic activity. In addition to this, if the second zeolite crystal having the molecular sieving effect forms a continuous phase matrix, the permeation resistance of a selected molecule becomes too large, which tends to decrease the molecular sieving effect. Moreover, since the second zeolite crystal serves as a binder (carrier) without the use of any binder (carrier) for shape retention, a zeolite bound zeolite catalyst with the first zeolite crystal aggregated by the second zeolite crystal, or a clumped zeolite bound zeolite catalyst will be obtained. It is considered that said aggregated or clumped catalyst requires shaping or sizing in use. In this case, however, the second zeolite crystal will be peeled off due to shear and fracture, which produces a part at which the first zeolite crystal is exposed, resulting in a decreased molecular sieving effect.

In addition, Patent Document 2 listed below discloses a method for coating solid acid catalyst particles with zeolite crystals having a molecular sieving effect. According to this method, however, each catalyst particle is relatively large with an average particle size of 0.3-3.0 mm and has a thick coating layer with a thickness of 1-100 μm. Therefore, it is believed that a body to be treated, such as the raw material and product, experiences a large resistance when passing through a silicate film, which results in an insufficient reaction efficiency, low conversion of toluene and significantly low yield of paraxylene. On the other hand, if the thickness of the coating film is reduced, the coating may be damaged due to physical damage, etc.

Furthermore, Patent Document 3 listed below discloses a catalyst that comprises a core made of crystalline borosilicate and a shell made of silicon oxide (crystalline silicate) having the same crystalline structure as the core. However, this catalyst indeed defines a weight ratio of shell/core in relation to the crystalline silicate of the shell, but there is no reference to the thickness, uniformity, defects or the like of silicate which determines reaction results. Additionally, no definition is provided as to the particle size or crystallite size for the crystalline borosilicate of the core. Such a catalyst would bring about incomplete formation of a silicate coating film, thereby significantly decreasing reaction activity. Otherwise, since a part of the outer surface of the core zeolite is exposed, it is difficult to achieve a reaction with highly controlled selectivity as is the case for obtaining high purity paraxylene.

In addition, Patent Document 4 listed below discloses a catalyst that is formed by coating MFI type zeolites having a particle size of not more than 100 μm with a crystalline silicate, and teaches that the catalyst coated with the crystalline silicate exhibits extremely high paraxylene selectivity and that a para-substituted aromatic hydrocarbon may be produced in an efficient manner as compared with the prior art. However, the reaction rate under the conditions described in Patent Document 4 is not adequate for commercialization. It is desired to develop a catalyst that has a higher reaction rate.

PRIOR ART DOCUMENTS

Patent Documents

Patent Document 1: JP-A-2001-504084
Patent Document 2: JP-A-2003-62466
Patent Document 3: JP-B-H01-006816
Patent Document 4: WO2009/119725A

SUMMARY OF THE INVENTION

Problem to be Solved by the Invention

As stated above, the prior art does not provide any catalyst that is useful for producing high purity paraxylene in an efficient manner without undergoing any complicated process, such as an isomerization process and/or an adsorption and separation process. Patent Document 4 is the only one that suggests the possibility. However, the reaction rate provided by Patent Document 4 is low relative to the existing toluene disproportionation processes and so on and further improvements in performance are still required for commercialization.

Generally, it is a common practice to achieve improved selectivity when selectively synthesizing paraxylene by suppressing the surface activity, such as by coating surfaces with inert components and by supporting components that are inert for isomerization reaction. In this case, however, a problem arises that the conversion rate is lowered. Thus, a high selectivity catalyst has a technical problem that the reaction conversion rate should necessarily be lowered. The inventors estimated that microparticulation of the catalyst would be most effective for solving this problem. However, while it was easy to apply coating to large zeolite particles (of around 10 µm or more), it was difficult to apply uniform and thin surface coating to microparticles of 3 µm or less.

Figure 1:
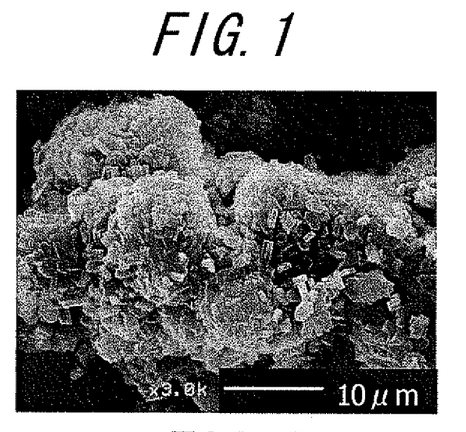
[FIG. 1] shows a scanning electron micrograph of an example of a catalyst where a core made up of fine-grained crystal and a coating layer are unconformable/unlinked.
Figure 2:
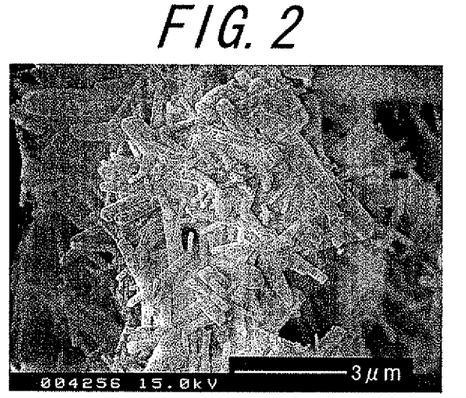
[FIG. 2] shows a scanning electron micrograph of another example of a catalyst where a core made up of fine-grained crystal and a coating layer are unconformable/unlinked.
Figure 3:
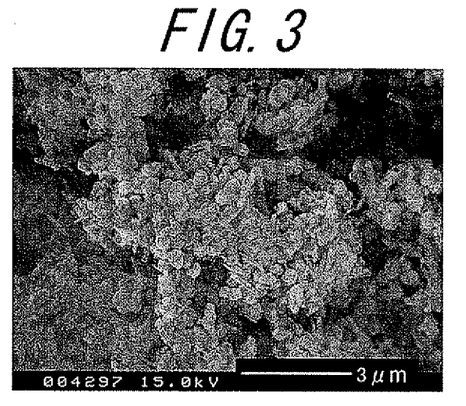
[FIG. 3] shows a scanning electron micrograph of still another example of a catalyst where a core made up of fine-grained crystal and a coating layer are unconformable/unlinked.

The inventors have made various investigations of the causes and found the following: those microparticles for which the coating process was not successfully completed have surfaces such that crystal faces are coarse and many fine-grained (as might be crystalline nuclei) microparticles are adhered thereto, which leads to generation of a large number of crystals of scaly or fine acicular particles (see FIGS. 1-3), in which case the coating process itself succeeds, but is far from the implementation of the intended uniform and thin surface coating, which contribute to the causes that interfere with improving catalytic activity per unit volume or per unit weight.

The present invention has been accomplished in view of the above circumstances. An object of the present invention is to provide a novel catalyst that has a molecular sieving effect (or shape selectivity) and better catalytic activity and a method for producing the same, as well as a method that allows efficient production of high purity paraxylene by using the catalyst, without performing an isomerization process and/or an adsorption and separation process.

Means for Solving the Problem

The inventor has made various studies and as a result arrived at an innovative method for producing paraxylene whereby separation is facilitated by preparing a catalyst that is optimum for the above-described object. Specifically, the inventors have found that a catalyst may be prepared and used to solve the problem by microparticulating zeolite of the core of the catalyst that predominates in the reaction and at the same time smoothing the crystalline surface thereof, and further eliminating adhesion of fine particles that would otherwise interfere with uniform crystal growth, followed by allowing uniform crystal growth on the zeolite of the core while controlling the aluminum concentration. According to the present invention, since only those isomers having a particular structure in the product produced in the catalyst particles are selectively allowed to pass through a zeolite film having a molecular sieving effect, it is possible to improve the selectivity of isomers having a particular structure, and conversely, it is also possible to induce a selective (specific) reaction within catalyst particles so that only those isomers having a particular structure are allowed to selectively enter into catalytically active catalyst particles. As a result, high purity paraxylene may be produced in an efficient manner according to the present invention.

That is, the present invention provides (1) a catalyst comprising: a core made of a zeolite particle having a particle size of 10 µm or less, preferably 3 µm or less, more preferably 1 µm or less; and a zeolite layer covering the core, wherein as measured by X-ray photoelectron spectroscopy, an outermost surface of the catalyst has a silica/alumina molar ratio of not less than 800, the core made of the zeolite particle has an average silica/alumina molar ratio of not more than 300, and the zeolite layer has an aluminum concentration increasing inward from an outer surface of the catalyst.

In the catalyst of the present invention, as measured by X-ray photoelectron spectroscopy, an outermost surface of the catalyst has a silica/alumina molar ratio of not less than 800, preferably not less than 1000, and the core made of the zeolite particle has an average silica/alumina molar ratio of not more than 300, preferably not more than 100, more preferably not more than 50. Where the silica/alumina molar ratio of the outermost surface indicates a silica/alumina molar ratio from the outer surface to a depth of 4.2 nm as measured by X-ray photoelectron spectroscopy, and an average silica/alumina molar ratio of the core is determined by composition analysis in accordance with ICP emission spectrophotometry.

In addition, in the catalyst of the present invention, (2) a thickness of the zeolite layer covering the core is preferably not less than 10 nm but not more than 1 µm.

In addition, in the catalyst of the present invention, (3) the zeolite particle as the core and the zeolite layer covering the core preferably have an MFI structure, and the zeolite layer is preferably epitaxial to the zeolite particle as the core.

As used herein, epitaxy is a phenomenon where a particular surface of a certain crystal grows on a particular surface of another crystal in apparently attached and overlapping relationship with each other, as described in *Kagaku Daijiten* (*Chemical Dictionary*) compact edition vol. 1, edited by Kagaku Daijiten Editorial Committee, 36th impression, Kyoritsu Shuppan Co., Ltd., Sep. 20, 1997, pp. 961-962. For isomorphic crystals, growth occurs in such a direction as to share a common crystalline axis. That is, epitaxy in the present application means a condition where a coating layer having the same structure as that of MFI type zeolite as the core (inner core) forms a crystalline phase that is continuous with the crystalline phase as the core (inner core), and where pores in both phases are continuous. This condition is achieved by using hydrothermal synthesis, as described below, to allow the same crystalline layer to grow on the surface of MFI type zeolite as the core (inner core).

The present invention also provides (4) a method for producing a catalyst, wherein a zeolite particle containing aluminum and having a particle size of not more than 10 μm, preferably 3 μm, more preferably 1 μm, is provided as a core and subjected to hydrothermal synthesis using a silica source, an aluminum source and a structure directing agent so that a zeolite layer having the same crystalline structure as the zeolite particle is precipitated on an outer surface of the zeolite particle as the core, and the method comprising: performing hydrothermal synthesis while adding the silica source in a continuous or intermittent manner, and causing crystal growth of the zeolite layer on a surface of the zeolite particle as the core while decreasing an aluminum concentration in a synthesis solution.

Here, the structure directing agent means a reagent that determines a zeolite structure (e.g., MFI) at the time of hydrothermal synthesis, which is also referred to as a template or a mold molecule and is usually an organic compound of quaternary ammonium type, as illustrated in *R. F. Lobo et al., Phenomena and Molecular Recognition in Chem.*, 21, 47 (1995).

Further, the present invention provides (5) a method for producing paraxylene, wherein alkylation or disproportionation reaction is performed by contacting the catalyst according to any one of (1)-(3) described above with benzene and/or toluene.

Effect of the Invention

The outermost surface of the catalyst of the present invention contains little or no aluminum and does not have paraxylene synthesis activity and paraxylene isomerization activity. On the other hand, the catalyst of the present invention has an aluminum concentration increasing toward the inner part of each particle from an outer surface of the catalyst and thereby improves paraxylene synthesis activity. However, in the inner part of each particle, paraxylene isomerization activity and diffusion rate of other isomers are significantly reduced due to the shape selectivity of zeolite. Consequently, the catalyst of the present invention may be preferably used to selectively produce an isomer having a particular structure, such as paraxylene.

BRIEF DESCRIPTION OF THE DRAWINGS

[FIG. 5-1] shows a scanning electron micrograph of Catalyst A;

[FIG. 5-2] shows another scanning electron micrograph of Catalyst A;

BEST MODE FOR CARRYING OUT THE INVENTION

[Catalyst]

The catalyst according to the present invention comprises: a core made of the zeolite particle having a particle size of not more than 10 μm, preferably not more than 3 μm, more preferably not more than 1 μm; and a zeolite layer covering the core, wherein the zeolite layer has an aluminum concentration increasing inward from an outer surface of the catalyst, and wherein the zeolite layer covering the core preferably has a thickness of not less than 10 nm but not more than 1 μm.

Preferably, the zeolite particle used as the core of the above-described catalyst is a zeolite having an MFI structure. The zeolite having an MFI structure shows superior catalyst performance for producing paraxylene in a structurally selective manner upon reaction with an aromatic hydrocarbon or with an aromatic hydrocarbon and an alkylating agent. Preferably used as the MFI type zeolites are various silicate materials, such as ZSM-5, TS-1, TSZ, SSI-10, USC-4, NU-4 and so on. These zeolites can distinguish paraxylene from orthoxylene or metaxylene having a molecular size slightly larger than that of paraxylene. This is because they have a pore size of around 0.55 nm which is as large as the minor axis of paraxylene molecule, and are effective in the case of producing target paraxylene.

The above-described zeolite particle as the core of the catalyst has a particle size of not more than 10 μm, preferably not more than 3 μm, more preferably not more than 1 μm, particularly preferably not more than 0.5 μm, and preferably not less than 0.1 μm. As the zeolite particle used has a smaller particle size, it is more desirable because the influence of pore diffusion may be reduced. For zeolite particles of less than 0.1 μm, however, it is more difficult to provide uniform coating of the outer surface with the zeolite layer (crystalline aluminosilicate layer) due to aggregation among particles and so on. This also causes a significant reduction in production efficiency in steps such as a filtering/washing, which is thus considered unfavorable. On the other hand, for zeolite particles having a particle size of more than 10 μm, the reaction substance (raw material) is diffusion-limited in the particles and the mole number of active species per volume in the vicinity of the outer surface which contributes to reaction is small. This results in a significant reduction in the conversion rate of reaction. Thus, such zeolite particles are not industrially feasible. It should be noted that particle size may be measured using a particle size distribution meter, a scanning electron microscope (SEM), or the like.

In addition, the above-described zeolite particle has a silica/alumina ratio of preferably not less than 20, more preferably not less than 25, still more preferably not less than 30. In addition, the above-described zeolite particle has a silica/alumina ratio of preferably not more than 300, more preferably not more than 100, most preferably not more than 50. For a given silica/alumina ratio of less than 20, it is difficult to keep the MFI structure stable, whereas above 300, there is a small amount of acids corresponding to reaction active sites, which is considered unfavorable because the reaction activity decreases.

The catalyst of the present invention is such a catalyst that comprises a core made of the zeolite particle having a particle size of not more than 10 μm, preferably not more than 3 μm, and a zeolite layer covering the core, and that has a composition distribution such that the zeolite layer has an aluminum concentration increasing, preferably monotonically increasing, inward from an outer surface of the catalyst, wherein the zeolite layer covering the core has a thickness of preferably not less than 10 nm but not more than 1 μm. In the catalyst of the present invention, it is also preferable that both the zeolite particle as the core (inner core) and the zeolite layer covering the core have an MFI structure and the zeolite layer is epitaxial to the zeolite particle as the core. That is, it is preferable that the zeolite layer in the vicinity of this outer surface also has a molecular sieving effect and is continuous with the pores of the MFI type zeolite of the core. This structure may suppress pore blockage caused by formation of a coating layer in the vicinity of the outer surface or a decrease in catalytic activity due to diffusion resistance. In addition, it is possible to reduce the thickness of the coating layer that may achieve the required shape selectivity. Besides, methods for ascertaining continuity of pores include a method for measuring diffusion rates of hydrocarbons having different molecule sizes or for determining whether pores are permeable and so on.

It should be noted that the condition of the crystalline surface of the underlying core is important for forming an epitaxial crystalline structure. For developing a high performance catalyst, firstly, zeolite microparticles that are catalytic active species and are used as the core (inner core), preferably such zeolite microparticles that have a particle size of not more than 3 μm are synthesized. At this moment, synthesis conditions are preferably set in such a way that zeolite particles are generated in such a form as to allow application of smooth, uniform and thin surface coating to the surfaces of microparticles. For example, crystals having almost spherical shape and smooth surfaces may be obtained by controlling the hydrothermal synthesis condition at around pH=11 to 12.5. It is also preferable to remove excess microparticles by performing operations such as centrifugation and washing after the synthesis/crystallization process, in order to prevent any small $SiO_2$ particles (or zeolite precursors) generated at the same time in the crystalline synthesis from being adhered to the surfaces of these microparticles and thereby disturbing the smooth crystalline surfaces.

Following this synthesis operation of microparticles, the microparticles may be immersed in a Si-rich (Al-poor) crystal growth liquid for hydrothermal synthesis, which allows a silica-rich crystal to be generated on a surface of a seed crystal. At this moment, it is important to grow crystals by initially contacting the microparticles with a hydrothermal synthesis solution containing a large amount of Al (which may be an Al component eluted from a surface of the seed crystal in a strong alkaline solution), and then gradually and continuously or else intermittently adding a solution containing a Si source thereto so that the Al concentration in the solution gradually decreases. This method allows gradual increase of the Si/Al ratio in the zeolite layer generated on the surface. In this case, if the Si/Al ratio is rapidly increased, then crystal growth does not occur uniformly; possibly no crystal growth occurs on the seed crystal and silicalite is precipitated independently, which hinders production of the target catalyst.

As a specific method for adding a Si source, it is preferable to add a Si source corresponding to 5% to 1000%, preferably 10% to 400%, more preferably 30% to 200% by weight of $SiO_2$, based on the zeolite crystal as the core, over 5 hours or more, preferably 12 hours or more, more preferably 24 hours or more, in a slow and continuous or else intermittent manner. While the hydrothermal synthesis temperature at this moment is extremely important as it is a factor that determines the crystallization rate of Si, temperatures of preferably 90° C. to 250° C., more preferably 110° C. to 180° C. are used depending on the ratio of the amount of the Si source added.

In addition, it is desirable that the zeolite layer in the vicinity of the outer surface is inert for disproportionation reaction and alkylation reaction at least in the outermost surface, and it is particularly preferred that the zeolite layer is made of pure silica zeolites containing no alumina component (silicalite-1). Silicalite-1 is particularly preferred because it has little acid sites and thus does not facilitate the catalytic reaction in the outer surface. It should be noted that silicon in the pure silica zeolite film (silicate) may be partially replaced with another element, such as gallium, germanium, phosphorus, boron or the like. Again, it is still important to keep the surface inert for any side reaction of the target reaction.

In the catalyst of the present invention, the zeolite layer in the vicinity of the outer surface has a thickness of not less than 10 nm but not more than 1 μm, preferably 20 to 500 nm, particularly 50 to 200 nm. If the above-described zeolite layer in the vicinity of the outer surface has a thickness of less than 10 nm, then the MFI type zeolite as the core (inner core) and the outer surface-modified layer are liable to be unconformable with each other, which may result in not only an inability to maintain the catalytic activity at a high level, but also in an increase in the likelihood that modification involves defects, interfering with full use of the molecular sieving effect. On the other hand, if the zeolite layer in the vicinity of the outer surface has a film thickness of more than 1 μm, then the zeolite layer in the vicinity of the outer surface becomes too thick. Consequently, the raw material, product and so on experience an excessively large resistance when passing through the layer, which is considered unfavorable because the conversion rate of reaction is lowered. In this case, the thickness of the zeolite layer in the vicinity of the outer surface may be calculated from the difference between the particle size of the zeolite particle and the particle size of the catalyst obtained by coating the core made of the zeolite particle with the zeolite layer. In addition, the silica/alumina molar ratio of the zeolite layer in the vicinity of the outer surface may be measured by the following method.

Information about the composition in the 2-5 nm vicinity of the outer surface is obtained using an X-ray photoelectron spectrometer (XPS). This information regarding the vicinity of the outer surface may be obtained by so-called angle-resolved XPS analysis where the escape depths of detectable photoelectrons may be changed by changing the takeoff angles of the photoelectrons emitted upon irradiation with X-rays. Information regarding the deeper positions is obtained by cutting out a surface of a particle by etching, abrasion and so on, and applying the (angle-resolved) XPS analysis again. In the present application, the results of composition analysis up to a takeoff angle of 45°, i.e., a depth of 4.2 nm, which is an analysis condition with a standard X-ray photoelectron spectrometer (XPS), is assumed as the results of composition analysis of the zeolite layer in the vicinity of the outer surface. In the present application, analysis data in the depth direction of a particle was obtained by analyzing the composition of the surface (up to takeoff angle 45°=4.2 nm deep) each time removing a crystalline particle in the middle of the hydrothermal synthesis with an X-ray photoelectron spectrometer (XPS).

Specifically, under the conditions considered in the present application, the following escape depths were obtained for respective takeoff angles. Besides, measurement targets were obtained by press-molding samples (powder).

<Analysis Conditions>
Device: 5600MC, manufactured by ULVAC-PHI, Incorporated
Attainable Vacuum: $6.9 \times 10^{-8}$ Torr
Excitation Source MgKα
Output: 400 W
Detection Area: 800 μmφ
Incident Angle: 45°
Takeoff Angle: 15° to 60° (Angle-Resolved Measurement)
Neutralizer gun used

TABLE 1

| |
| --- |
| takeoff angle = 15°; about 1.6 nm |
| takeoff angle = 20°; about 2.1 nm |
| takeoff angle = 45°; about 4.2 nm |
| takeoff angle = 60°; about 5.2 nm |

In the catalyst of the present invention, as measured by X-ray photoelectron spectroscopy, an outermost surface of the catalyst has a silica/alumina molar ratio of not less than 800, preferably not less than 1000, and the core made of the zeolite particle has an average silica/alumina molar ratio of not more than 300, preferably not more than 100. If the outermost surface has a silica/alumina molar ratio of not less than 800 as measured by X-ray photoelectron spectroscopy, the outermost surface of the catalyst has little acid sites, without facilitating catalyst reaction in the outermost surface, e.g., disproportionation reaction, alkylation reaction and isomerization reaction, which is thus considered preferable. In addition, if the core made of the zeolite particle has an average silica/alumina molar ratio of not more than 300, then there is a sufficient amount of acid sites in the catalyst, allowing paraxylene to be generated selectively at an adequate reaction rate.

In the present invention, preferred as a method for controlling the composition of the zeolite layer in the vicinity of the outer surface of the zeolite particle is a scheme for performing hydrothermal synthesis while additionally loading a Si raw material in a continuous manner. Firstly, for example, used as the Si raw material are formless silica, amorphous silica, fumed silica, colloidal silica, tetraethyl orthosilicate (TEOS) and so on. These silica sources as well as a structure directing agent such as tetrapropyl ammonium hydroxide, a mineralizer such as a hydroxide of an alkali metal or alkaline-earth metal and so on are dissolved in water or ethanol to prepare an aqueous solution or sol for hydrothermal synthesis. Here, using an appropriate ratio of a silica raw material and a structure directing agent enables formation of an appropriate zeolite layer. In order to achieve uniform crystal growth without unevenness on the surface of the zeolite particle as the core, an aluminum source such as aluminum nitrate or sodium aluminate may be added at the beginning of coating synthesis. In addition, in order to reduce the aluminum concentration in the coating synthesis liquid to control the concentration of the liquid, such a method is also effective where any supernatant liquid is extracted, along with additional loading of a Si raw material, subsequent to the solid-liquid separation process, such as centrifugal separation and decantation.

While any silicate, such as Aerosil, fumed silica, Cabosil and so on, is preferably used as a silica raw material, a preferred raw material is the one from which ultrafine silica particles are easily formed, including tetraalkoxysilanes such as tetraethyl orthosilicate, tetramethyl orthosilicate and tetraisopropyl orthosilicate, colloidal silica and so on. The silica raw material has an average particle size of preferably not less than 1 nm but less than 1.0 μm, more preferably not less than 3 nm but less than 0.5 μm, for the purpose of appropriately controlling the rate at which silica is eluted into the hydrothermal synthesis solution. If the silica raw material has an average particle size of less than 1 nm, then the dissolution rate becomes excessively large, which results in an accelerated crystal precipitation rate and causes crystallization or precipitation among silica sources. As a result, the silica raw material is no longer available for coating, which is thus considered unfavorable. On the other hand, if the silica raw material has an average particle size of not less than 1.0 μm, then the dissolution rate becomes small and formation of a zeolite coating layer becomes very slow, which is thus considered unfavorable.

In addition, preferred as a structure directing agent is a quaternary ammonium salt, such as tetrapropyl ammonium hydroxide, tetraethyl ammonium hydroxide, tetrapropyl ammonium bromide and so on.

Preferably, the above-described hydrothermal synthesis solution for forming a zeolite coating layer has a pH of not less than 9 but less than 13. If the aqueous solution has a pH range other than said pH range, then the formation reaction of a zeolite coating layer does not progress sufficiently, which is thus considered unfavorable.

Next, the individual surfaces of the zeolite particles are processed with the aqueous solution for forming the zeolite coating layer by immersing the zeolite particles as the core in said aqueous solution for forming the zeolite coating layer, or applying said aqueous solution for forming the zeolite coating layer to each of the zeolite particles as the core. Then, hydrothermal treatment is carried out to form a zeolite coating layer over the entire surface of each zeolite particle.

Said hydrothermal treatment may be performed by immersing in heated water, or leaving in heated water vapor, the zeolite particles of the core processed with the hydrothermal synthesis solution for forming a zeolite coating layer. Specifically, the zeolite particles of the core may be heated in an autoclave while being immersed in the aqueous solution for forming a zeolite layer, or a heat-resistant airtight vessel containing the zeolite particles of the core and the aqueous solution for forming a zeolite coating layer may be directly placed and heated in an oven.

Said hydrothermal treatment is performed at temperatures of preferably not less than 90° C. but not more than 250° C., more preferably not less than 110° C. but not more than 180° C., and for preferably not less than 0.5 hour but not more than 72 hours, more preferably not less than 1 hour but not more than 48 hours. This hydrothermal treatment is repeated once to ten times as needed. At this moment, a Si source is gradually added to gradually decrease the aluminum concentration in the aqueous solution. In addition, instead of repeating such hydrothermal treatment, addition of the Si source may be performed in a continuous or intermittent manner in the middle of the hydrothermal synthesis. At this moment, following the solid-liquid separation process such as centrifugal separation and decantation, any supernatant liquid may be extracted to decrease the aluminum concentration in the hydrothermal synthesis solution. With this hydrothermal synthesis process, a zeolite coating layer with a controlled aluminum concentration gradient may be epitaxially grown on the zeolite crystals of the core.

After the hydrothermal treatment, the obtained zeolite catalyst is removed and dried, and further subjected to heat treatment to calcine and eliminate the structure directing agent and so on. The calcination may be performed by increasing the temperature at a rate of temperature rise of 0.1-10° C./min as needed, followed by heat treatment at temperatures between 500 and 700° C. for 0.1-10 hours. After the calcination process, if necessary, an ion exchange process may be performed to reduce/eliminate any alkali metal components such as Na, or to introduce various transition metal elements for enhanced performance.

Usually, this kind of catalyst is molded for use. While various molding schemes are conceivable, tumbling granulation, press molding, extrusion molding and so on are specifically preferred, because this catalyst needs to be molded without damaging the surface zeolite coating layer. In molding, if necessary, various organic or inorganic binders and molding aids may also be used.

[Disproportionation/Alkylation of Aromatic Hydrocarbon]

The method for producing paraxylene according to the present invention is characterized in that paraxylene is produced selectively through reaction (disproportionation) among aromatic hydrocarbons or reaction (alkylation) between an aromatic hydrocarbon and an alkylating agent, in the presence of the above-mentioned catalyst.

Aromatic hydrocarbons as raw materials include benzene and toluene. Aromatic hydrocarbons as raw materials may include hydrocarbon compounds other than benzene and toluene. However, as paraxylene is the target product, those containing metaxylene, orthoxylene and ethylbenzene are not preferred as raw materials.

Alkylating agents used in the present invention include methanol, dimethyl ether, dimethyl carbonate, methyl acetate and so on. While commercially available agents may be used, for example, methanol or dimethyl ether which is produced from a synthesis gas as a mixed gas of hydrogen and carbon monoxide, or dimethyl ether which is produced by dehydration reaction of methanol may also be a starting material. Besides, impurities that may be present in benzene, toluene, methanol and dimethyl ether include water, olefin, sulfur compounds and nitrogen compounds; less impurities are preferred.

A ratio of alkylating agents to aromatic hydrocarbons in the above-described alkylation reaction is preferably between 5/1 and 1/20, more preferably between 2/1 and 1/10, particularly preferably between 1/1 and 1/5, as a molar ratio of methyl group to aromatic hydrocarbon. If the alkylating agents are present in an extremely large amount relative to the aromatic hydrocarbons, then undesirable reaction among the alkylating agents progresses and at the same time the likelihood of inducing coking that would lead to degradation of the catalyst increases, which is thus considered unfavorable. Alternatively, if the alkylating agents are present in an extremely small amount relative to the aromatic hydrocarbons, then the conversion rate of the alkylation reaction to aromatic hydrocarbons is significantly lowered. In addition, if toluene is used as an aromatic hydrocarbon, disproportionation reaction among toluenes progresses.

It is desirable that the above-described disproportionation reaction or alkylation reaction is performed by supplying aromatic hydrocarbons of raw materials at a liquid hourly space velocity (LHSV) of not less than 0.01 $h^{-1}$, more preferably not less than 0.1 $h^{-1}$, but not more than 10 $h^{-1}$, more preferably not more than 5 $h^{-1}$ so that the aromatic hydrocarbons come in contact with the above-mentioned catalyst. The reaction conditions of disproportionation reaction or alkylation reaction include, but not limited to: reaction temperatures of preferably not less than 200° C., more preferably not less than 230° C., particularly preferably not less than 250° C., but preferably not more than 550° C., more preferably not more than 530° C., particularly preferably not more than 510° C.; and pressures preferably equal to or greater than atmospheric pressure, more preferably not less than 0.1 MPaG, particularly preferably not less than 0.5 MPaG, but preferably not more than 20 MPaG, more preferably not more than 10 MPaG, still more preferably not more than 5 MPaG.

At the time of disproportionation reaction or alkylation reaction, it is also possible to circulate or pressurize an inert gas such as nitrogen and helium or hydrogen for suppressing coking. Besides, if the reaction temperature is too low, then the conversion rate of the raw material aromatic hydrocarbons is low due to insufficient activation of aromatic hydrocarbons and alkylating agents; whereas if the reaction temperature is too high, then the lifetime of the catalyst tends to be shortened, in addition to a large consumption of energy.

In the presence of the above-described catalyst, as methylation reaction or disproportionation reaction of toluene progresses, the following are assumed to be generated in addition to paraxylene of the target product: orthoxylene, metaxylene and ethylbenzene, which are structural isomers; unreacted toluene; alkylbenzenes having a carbon number of not less than 9, for which methylation has progressed; and light gases. Here, among the aromatic hydrocarbons having a carbon number of 8, a higher component ratio of paraxylene is preferred. At the first stage process of this reaction, 85 mol % or more is preferable, 95 mol % or more is more preferable, 99 mol % or more is still more preferable, 99.5 mol % or more is particularly preferable and 99.9 mol % or more is most preferable.

While the reaction product may be separated and concentrated by an existing method, a more efficient process is enabled even when using an existing method because paraxylene having an extremely high purity is selectively obtained according to the present invention. Particularly, for paraxylene having a high purity, such paraxylene can be isolated only by a simple distillation method. In addition, if high-boiling fractions are generated in an extremely small amount relative to paraxylene, then high purity paraxylene can be isolated only by distillation of light components. Besides, any unreacted toluene may be subjected to the reaction again as a raw material.

EXAMPLES

The present invention will be described in more detail with reference to examples given below. However, the present invention is not limited to the disclosed examples in any sense.

<Preparation of Zeolite Catalyst as Core>

(Preparation of Catalyst A)

Figure 4:
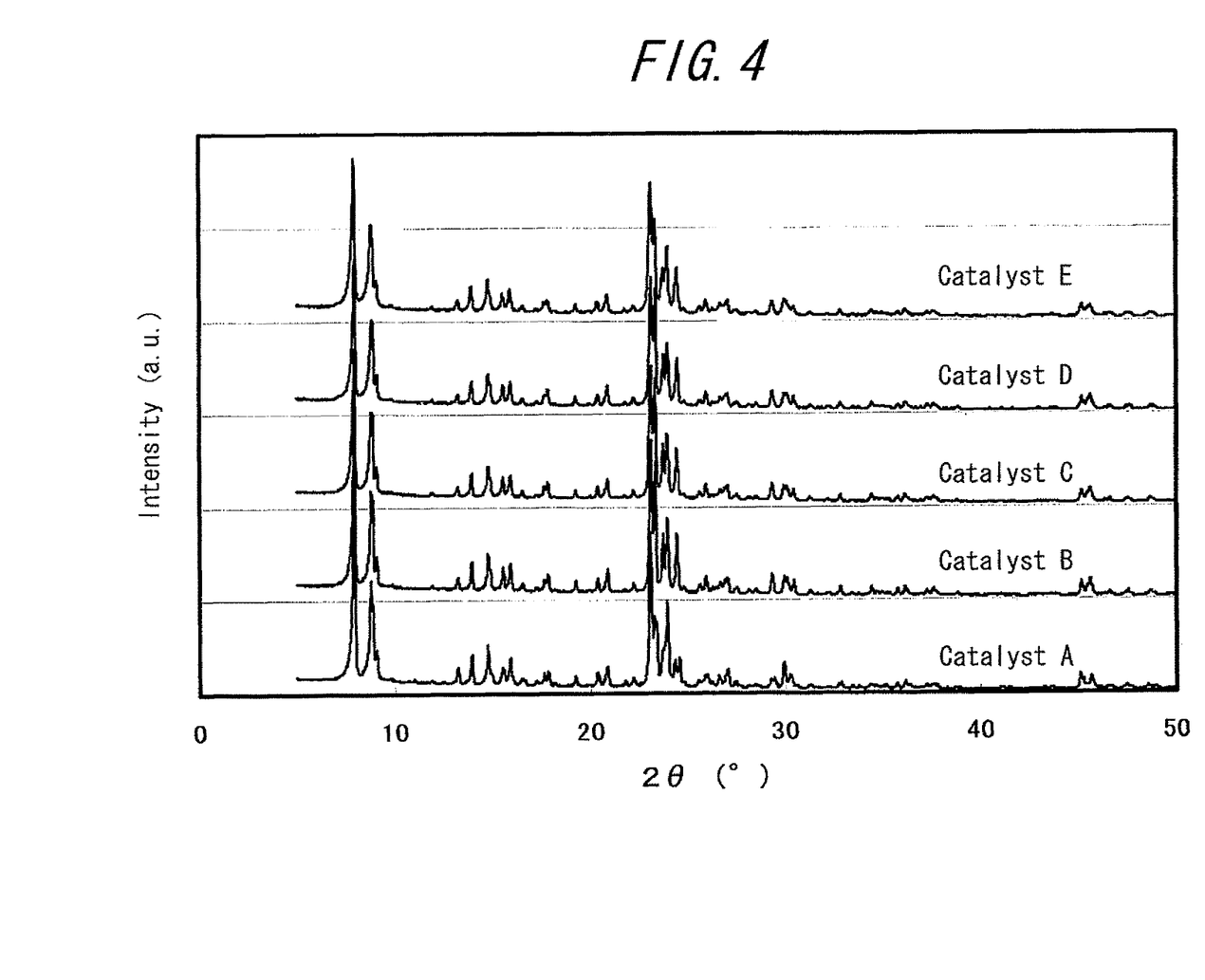
[FIG. 4] shows X-ray diffraction patterns of Catalyst A, Catalyst B, Catalyst C, Catalyst D and Catalyst E.
Figure 6:
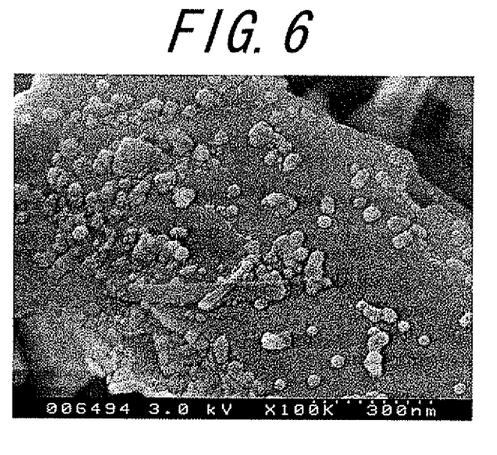
[FIG. 6] shows a scanning electron micrograph of Catalyst B.
Figure 7:
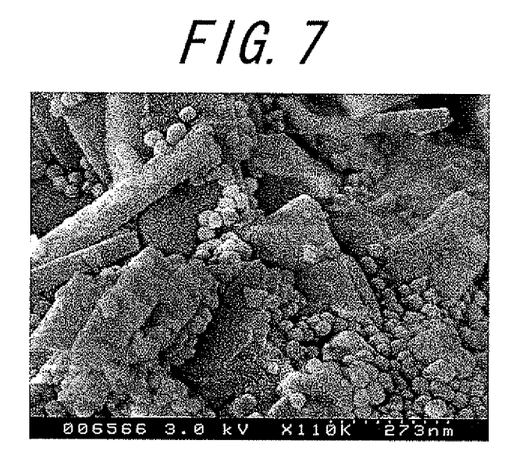
[FIG. 7] shows a scanning electron micrograph of Catalyst C.
Figure 8:
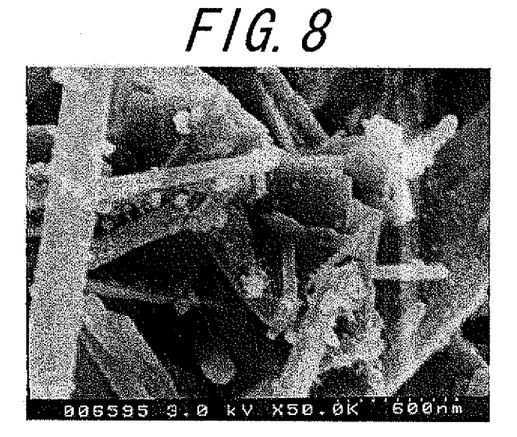
[FIG. 8] shows a scanning electron micrograph of Catalyst D.
Figure 9:
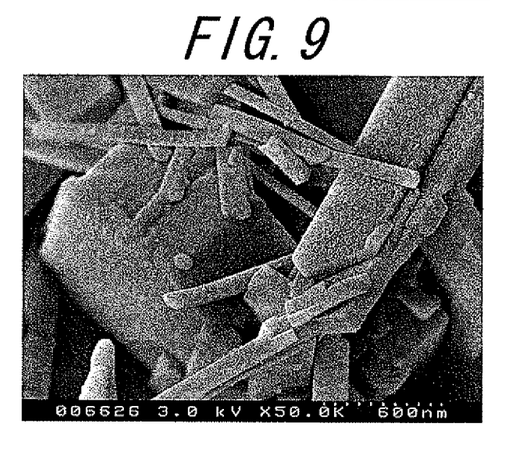
[FIG. 9] shows a scanning electron micrograph of Catalyst E.

As a silica source, 26.1 g of tetraethyl orthosilicate (TEOS) and 10.0 g of colloidal silica are collected, and as an aluminum source, 4.37 g of aluminum nitrate nonahydrate is collected. They are dissolved in 50.9 g of an aqueous solution of 10% tetra propyl ammonium hydroxide (TPAOH) and 29.3 g of ion exchange water. Further add about 10 g of 28% ammonia water for pH adjustment. The pH of the aqueous solution at this moment is 11.0. This aqueous solution is subjected to hydrothermal synthesis by being put into a hydrothermal synthesis vessel made of Teflon®, heated to a temperature of 110° C. at a rate of temperature rise of 1.4° C./min, maintained at the same temperature for 24 hours, then raised to a temperature of 180° C. over 36 hours, maintained at a temperature of 180° C. for 8 hours. The pH of the aqueous solution after the hydrothermal synthesis turns to 11.8. The average particle size of the obtained Sediment A is measured as 0.44 μm with a particle size distribution meter, MI-3000, manufactured by Nikkiso Co., Ltd. In addition, as a result of the X-ray diffraction analysis, the Sediment A is determined as MFI type zeolites having a crystallite size of 67 nm (see FIG. 4). On the other hand, the aluminum concentration in the residual liquid of the hydrothermal synthesis aqueous solution after removing the sediment therefrom is 520 ppm (0.52 g/L), Besides, it is determined from the result of the composition analysis that this crystal has a silica/alumina ratio ($SiO_2/Al_2O_3$ (molar ratio)) of 35. The obtained product is washed, filtered, dried and thereafter calcined at 550° C. for 2 hours, whereby Catalyst A is obtained. The composition of the outermost surface of the Catalyst A (takeoff angle 45°=4.2 nm deep) is measured with XPS as 29 in silica/alumina ratio ($SiO_2/Al_2O_3$ (molar ratio)).

In addition, the conditions of measurement of crystallite size are as follows:

Measuring Device: RAD-1C, manufactured by Rigaku Corporation

X-Ray Source: Cuká 1 (λ=0.15 nm)

Tube Voltage: 30 kV

Tube Current: 20 mA

Measurement Conditions Scan Rate: 4°/min

Step Width: 0.02°

Slit: DS=1.0°, RS=0.3 mm, SS=1.0°

(Preparation of Catalyst B)

As is the case with "Preparation of Catalyst A", the core is subjected to zeolite synthesis, whereby a synthetic aqueous solution containing the Sediment A is obtained. In this case, the obtained synthetic aqueous solution is subjected to centrifugal separation at 3000 rpm for 3 minutes, after which the supernatant liquid is removed therefrom. Newly added to the resultant synthetic aqueous solution is a coating solution which is obtained by blending 30.6 g of tetraethyl orthosilicate (TEOS), 7.11 g of a 10%-TPAOH aqueous solution, 25.8 g of ethanol and 86.1 g of ion exchange water. After sealed in a hydrothermal synthesis container again, the resultant synthetic aqueous solution is heated to 180° C. and subjected to hydrothermal synthesis at this temperature for 12 hours. The pH of the aqueous solution after the reaction is 11.9. Further, the process from centrifugal separation to hydrothermal synthesis is repeated once again, whereby Sediment B is obtained. The average particle size of the obtained Sediment B is measured as 0.51 μm. The thickness of the coating layer calculated from the particle size is 35 nm. In addition, as a result of the X-ray diffraction analysis, the Sediment B is determined as MFI type zeolites having a crystallite size of 70 nm (see FIG. 4). On the other hand, the aluminum concentration in the residual liquid of the hydrothermal synthesis aqueous solution after removing the Sediment B therefrom is 52 ppm (0.052 g/L). Besides, it is determined from the result of the composition analysis using the ICP emission spectrometry that the Sediment B has a silica/alumina ratio ($SiO_2/Al_2O_3$ (molar ratio)) of 59. The obtained product is washed, filtered, dried and thereafter calcined at 550° C. for 2 hours, whereby Catalyst B is obtained. The composition of the outermost surface of the Catalyst B (takeoff angle 45°=4.2 nm deep) is measured with XPS as 311 in silica/alumina ratio ($SiO_2/Al_2O_3$ (molar ratio)).

(Preparation of Catalyst C)

As is the case with "Preparation of Catalyst B", the core is subjected to the zeolite synthesis and to the coating process twice, whereby a synthetic aqueous solution containing the Sediment B is obtained. Here, as is the case with "Preparation of Catalyst B", the synthetic aqueous solution is further subjected to the coating process twice, whereby Sediment C is obtained. The pH of the aqueous solution after the reaction is 12.0. The average particle size of the obtained Sediment C is measured as 0.54 μm. The thickness of the coating layer calculated from the particle size is 50 nm. In addition, as a result of the X-ray diffraction analysis, the Sediment C is also determined as MFI type zeolites having a crystallite size of 71 nm (see FIG. 4). On the other hand, the aluminum concentration in the residual liquid of the hydrothermal synthesis aqueous solution after removing the Sediment C therefrom is 19 ppm (0.019 g/L). Besides, it is determined from the result of the composition analysis using the ICP emission spectrometry that the Sediment C has a silica/alumina ratio ($SiO_2/Al_2O_3$ (molar ratio)) of 68. The obtained product is washed, filtered, dried and thereafter calcined at 550° C. for 2 hours, whereby Catalyst C is obtained. The composition of the outermost surface of the Catalyst C (takeoff angle 45°=4.2 nm deep) is measured with XPS as 983 in silica/alumina ratio ($SiO_2/Al_2O_3$ (molar ratio)).

(Preparation of Catalyst D)

As is the case with "Preparation of Catalyst C", the core is subjected to zeolite synthesis, whereby a synthetic aqueous solution containing the Sediment C is obtained. Here, as is the case with "Preparation of Catalyst B", the synthetic aqueous solution is further subjected to the coating process twice, whereby Sediment D is obtained. The pH of the aqueous solution after the reaction is 11.8. The average particle size of the obtained Sediment D is measured as 0.62 μm. The thickness of the coating layer calculated from the particle size is 90 nm. In addition, as a result of the X-ray diffraction analysis, the Sediment D is also determined as MFI type zeolites having a crystallite size of 71 nm (see FIG. 4). On the other hand, the aluminum concentration in the residual liquid of the hydrothermal synthesis aqueous solution after removing the Sediment D therefrom is less than 1 ppm (0.001 g/L). Besides, it is determined from the result of the composition analysis using the ICP emission spectrometry that the Sediment D has a silica/alumina ratio ($SiO_2/Al_2O_3$ (molar ratio)) of 105. The obtained product is washed, filtered, dried and thereafter calcined at 550° C. for 2 hours, whereby Catalyst D is obtained. The composition of the outermost surface of the Catalyst D (takeoff angle 45°=4.2 nm deep) is measured with XPS as 1000 or more in silica/alumina ratio ($SiO_2/Al_2O_3$ (molar ratio)) (over 1000 cannot be measured due to the detection limit for Al).

(Preparation of Catalyst E)

As is the case with "Preparation of Catalyst D", the core is subjected to zeolite synthesis, whereby a synthetic aqueous solution containing the Sediment D is obtained. Here, as is the case with "Preparation of Catalyst B", the synthetic aqueous solution is further subjected to the coating process twice, whereby Sediment E is obtained. The pH of the aqueous solution after the reaction is 11.8. The average particle size of the obtained Sediment E is measured as 0.65 μm. The thickness of the coating layer calculated from the particle size is 105 nm. In addition, as a result of the X-ray diffraction analysis, the Sediment E is also determined as MFI type zeolites having a crystallite size of 83 nm (see FIG. 4). On the other hand, the aluminum concentration in the residual liquid of the hydrothermal synthesis aqueous solution after removing the Sediment E therefrom is less than 1 ppm (0.001 g/L). Besides, it is determined from the result of the composition analysis using the ICP emission spectrometry that the Sediment E has a silica/alumina ratio ($SiO_2/Al_2O_3$ (molar ratio)) of 122. The obtained product is washed, filtered, dried and thereafter calcined at 550° C. for 2 hours, whereby Catalyst E is obtained. The composition of the outermost surface of the Catalyst E (takeoff angle 45°=4.2 nm deep) is measured with XPS as 1000 or more in silica/alumina ratio ($SiO_2/Al_2O_3$ (molar ratio)) (over 1000 cannot be measured due to the detection limit for Al).

Figure 10:
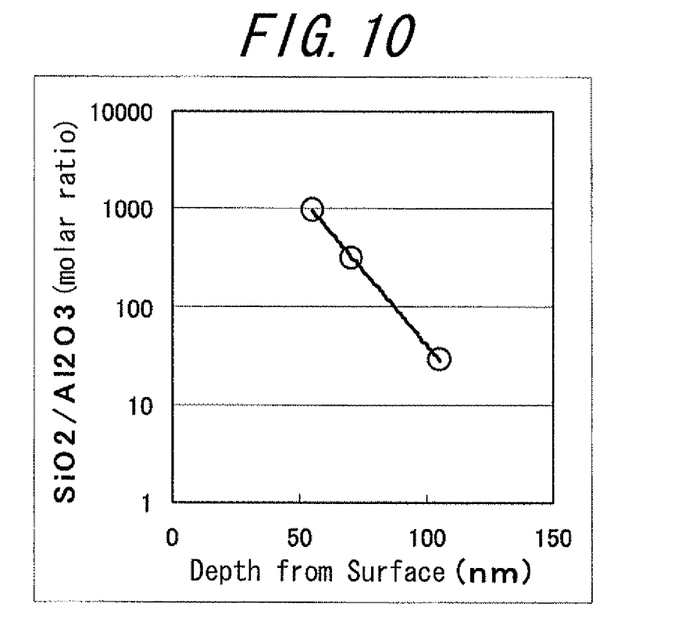
[FIG. 10] is a graph showing a relationship between the depth from the surface of Catalyst E and $SiO_2/Al_2O_3$ (molar ratio)
Figure 11:
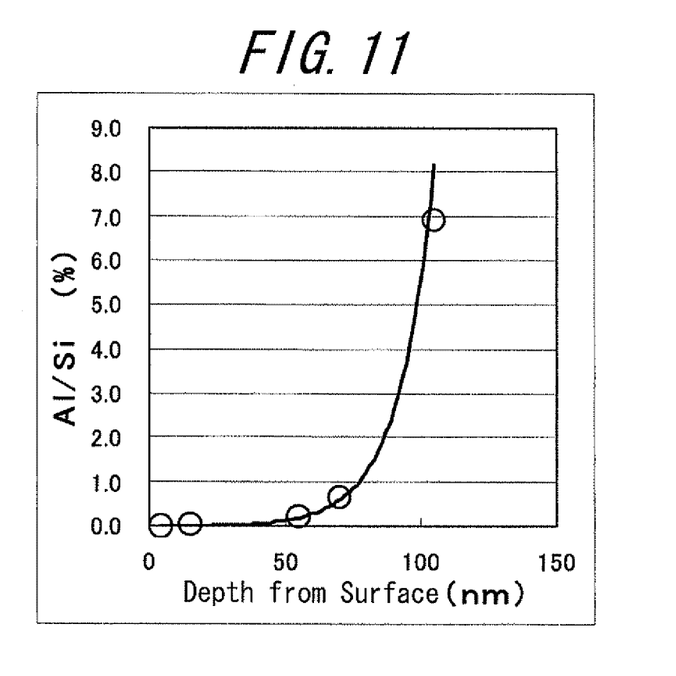
[FIG. 11] is a graph illustrating a relationship between the depth from the surface of Catalyst E and Al/Si (mol %).
Figure 51:
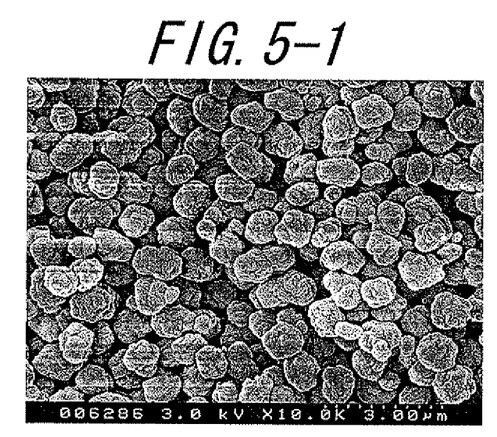
Figure 52:
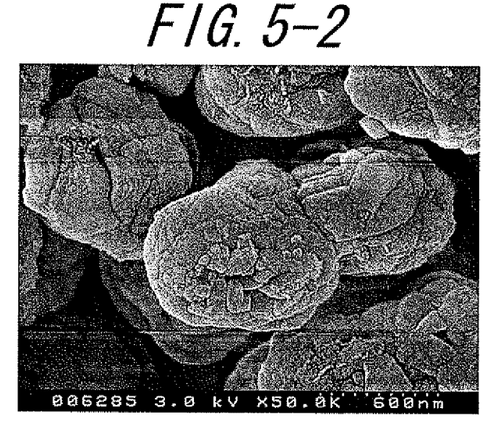

Based on the above-identified results (the particle size of each catalyst and the data of $SiO_2/Al_2O_3$ (molar ratio) on the surface with XPS; the results of particle growth and surface aluminum concentration for each particle size), the concentration distribution of aluminum of the finally-obtained Catalyst E in a depth direction is as illustrated in the graph of FIG. 10. It can be seen from FIG. 10 that $SiO_2/Al_2O_3$ (molar ratio) shows a sharp rise toward the vicinity of the outer surface. Thus, the concentration of aluminum drops as illustrated in FIG. 11. It can be understood from these results that the concentration of aluminum can be changed uniformly up to a depth of 100 nm, i.e., 0.1 μm, from the surface. On the other hand, since the present application advances crystallization of the outermost surface layer using a method for continuously is decreasing the aluminum concentration, no exfoliation or separation of the precipitated crystalline layer is found, although some isolated silicalite crystals are seen in SEM photographs.

<Disproportionation of Toluene>

Comparative Example 1

Silica (NIPGEL AZ-200, manufactured by Tosoh Silica Corporation) is added as a binder to the Catalyst A for molding (catalyst A/binder mass ratio=80/20), which in turn is sized in 16-24 mesh, and then 3.0 g of which is loaded into a fixed-layer reaction vessel having an inner diameter of 10 minϕ. Then, under the conditions of hydrogen partial pressure of 3 MPa, WHSV of 5.0 $h^{-1}$ and hydrogen/toluene ratio of 1.1 mol/mol, disproportionation reaction of toluene is carried out at 350° C., 400° C. and 450° C. The product at the reaction vessel outlet is analyzed by gas chromatography to obtain the generation ratio of different isomers. The results are shown in Table 2. The measurement conditions of gas chromatography are as follows:

Measuring Device: GC-2014, manufactured by Shimadzu Corporation

Column: capillary column Xylene Master, inner diameter of 0.32 mm, 50 m

Temperature Conditions; column temperature of 50° C., rate of temperature rise of 2° C./min, detector (FID) temperature of 250° C.

Carrier Gas: helium

Toluene Conversion(mol %)=100−(mol of residual toluene/mol of toluene in raw material)×100

Selectivity of Paraxylene in $C_8$(mol %)=(mol of generated paraxylene/mol of generated C8 aromatic hydrocarbon)×100

Paraxylene Yield(mol %)=(mol of generated paraxylene/mol of toluene in raw material)×100

Comparative Example 2

Disproportionation reaction of toluene is carried out under the same conditions as Comparative Example 1, except that the above-described Catalyst B is used as a catalyst. The measurement conditions of gas chromatography are also same as Comparative Example 1. The results are shown in Table 2.

Example 1

Disproportionation reaction of toluene is carried out under the same conditions as Comparative Example 1, except that the above-described Catalyst C is used as a catalyst. The measurement conditions of gas chromatography are also same as Comparative Example 1. The results are shown in Table 2.

Example 2

Disproportionation reaction of toluene is carried out under the same conditions as Comparative Example 1, except that the above-described Catalyst D is used as a catalyst. The measurement conditions of gas chromatography are also same as Comparative Example 1. The results are shown in Table 2.

Example 3

Disproportionation reaction of toluene is carried out under the same conditions as Comparative Example 1, except that the above-described Catalyst E is used as a catalyst. The measurement conditions of gas chromatography are also same as Comparative Example 1. The results are shown in Table 2.

TABLE 2

| | | | Reaction Temperature | | |
|---|---|---|---|---|---|
| | | | 350° C. | 400° C. | 450° C. |
| Comp. Ex. 1 | Catalyst A | Toluene Conversion (%) | 12.0 | 37.7 | 53.8 |
| | | Paraxylene Selectivity (%) | 25.6 | 24.2 | 22.8 |
| | | Paraxylene Yield (%) | 1.69 | 4.96 | 5.11 |
| Comp. Ex. 2 | Catalyst B | Toluene Conversion (%) | 5.0 | 20.4 | 47.7 |
| | | Paraxylene Selectivity (%) | 70.1 | 44.2 | 26.9 |
| | | Paraxylene Yield (%) | 1.98 | 4.96 | 6.01 |
| Ex. 1 | Catalyst C | Toluene Conversion (%) | 3.7 | 14.1 | 37.6 |
| | | Paraxylene Selectivity (%) | 86.8 | 66.3 | 41.1 |
| | | Paraxylene Yield (%) | 1.80 | 5.11 | 7.20 |
| Ex. 2 | Catalyst D | Toluene Conversion (%) | 2.6 | 9.6 | 25.9 |
| | | Paraxylene Selectivity (%) | 95.4 | 84.6 | 65.9 |
| | | Paraxylene Yield (%) | 1.40 | 4.44 | 7.87 |
| Ex. 3 | Catalyst E | Toluene Conversion (%) | 1.6 | 6.3 | 18.8 |
| | | Paraxylene Selectivity (%) | 98.8 | 94.3 | 83.4 |
| | | Paraxylene Yield (%) | 0.89 | 3.21 | 7.11 |

As described in Examples 1-3, it is apparent that by using the zeolite catalyst (Catalyst C, Catalyst D, Catalyst E) based on the present application as a catalyst, the selectivity of p-xylene becomes extremely high, such as not less than 85% (reaction temperature of 350° C.), as compared with the thermodynamic equilibrium composition (about 24%), and hence p-xylene is selectively produced. Also, in Example 3, since the selectivity of p-xylene is not less than 98%, the generated oil include only, in addition to toluene (with a boiling point of 110° C.) of the raw material, substantially, benzene (with a boiling point of 80° C.), paraxylene (with a boiling point of 138° C.) and traces of aromatic hydrocarbons (with a boiling point of 165-176° C.) having a carbon number of not less than 9. Therefore, high density paraxylene may be obtained by distillation.

On the other hand, it can be seen that in the case of using a catalyst having a higher surface aluminum concentration as indicated in Comparative Examples 1-2, the selectivity of paraxylene is significantly reduced relative to Examples 1-3.

The invention claimed is:

1. A catalyst comprising:
   a core made of a zeolite particle having an MFI structure and a particle size of not more than 10 μm; and
   a zeolite layer covering the core,
   wherein as measured by X-ray photoelectron spectroscopy,
   an outermost surface of the catalyst has a silica/alumina molar ratio of not less than 800,
   the core made of the zeolite particle has an average silica/alumina molar ratio of not more than 300, and
   the zeolite layer has an aluminum concentration increasing inward from an outer surface of the catalyst.

2. The catalyst according to claim 1, wherein a thickness of the zeolite layer covering the core is not less than 10 nm but not more than 1 μm.

3. The catalyst according to claim 1, wherein the zeolite layer covering the core has an MFI structure, and the zeolite layer is epitaxial to the zeolite particle as the core.

4. A method for producing the catalyst according to claim 1, wherein a zeolite particle containing aluminum and having a particle size of not more than 10 μm is provided as a core and subjected to hydrothermal synthesis using a silica source, an aluminum source and a structure directing agent so that a zeolite layer having the same crystalline structure as the zeolite particle is precipitated on an outer surface of the zeolite particle as the core, the method comprising:
   performing hydrothermal synthesis while adding the silica source in a continuous or intermittent manner, and
   causing crystal growth of the zeolite layer on a surface of the zeolite particle as the core while decreasing an aluminum concentration in a synthesis solution.

5. A method for producing paraxylene, wherein:
   an alkylation reaction is performed by contacting the catalyst according to claim 1 with benzene and/or toluene and an alkylating agent; or
   a disproportionation reaction is performed by contacting the catalyst according to claim 1 with toluene.

6. A method for producing paraxylene, wherein:
   an alkylation reaction is performed by contacting the catalyst according to claim 2 with benzene and/or toluene and an alkylating agent; or
   a disproportionation reaction is performed by contacting the catalyst according to claim 2 with toluene.

7. A method for producing paraxylene, wherein:
   an alkylation reaction is performed by contacting the catalyst according to claim 3 with benzene and/or toluene and an alkylating agent; or
   a disproportionation reaction is performed by contacting the catalyst according to claim 3 with toluene.

* * * * *